United States Patent
Ma et al.

(10) Patent No.: US 8,198,023 B2
(45) Date of Patent: Jun. 12, 2012

(54) PREVENTION AND ALLEVIATION OF STERIC HINDRANCE DURING SINGLE MOLECULE NUCLEIC ACID SYNTHESIS BY A POLYMERASE

(75) Inventors: Congcong Ma, Foster City, CA (US); Paul Wyatt, Foster City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 322 days.

(21) Appl. No.: 12/535,385

(22) Filed: Aug. 4, 2009

(65) Prior Publication Data
US 2010/0035269 A1    Feb. 11, 2010

Related U.S. Application Data

(60) Provisional application No. 61/086,404, filed on Aug. 5, 2008.

(51) Int. Cl.
*C12Q 1/68*    (2006.01)
*C12P 19/34*    (2006.01)

(52) U.S. Cl. ............... 435/6.1; 435/91.1; 435/91.2

(58) Field of Classification Search .......... 435/6.1, 435/91.1, 91.2
See application file for complete search history.

(56) References Cited

U.S. PATENT DOCUMENTS

| 5,270,184 A * | 12/1993 | Walker et al. ............. 435/91.2 |
| 5,418,149 A * | 5/1995 | Gelfand et al. ............. 435/91.2 |
| 5,547,839 A | 8/1996 | Dower et al. |
| 6,210,896 B1 | 4/2001 | Chan |
| 6,255,083 B1 | 7/2001 | Williams |
| 6,258,568 B1 * | 7/2001 | Nyren .......................... 435/91.1 |
| 6,787,308 B2 | 9/2004 | Balasubramanian et al. |
| 7,056,661 B2 | 6/2006 | Korlach et al. |
| 7,056,671 B2 * | 6/2006 | Enoki et al. ................... 435/6.12 |
| 2003/0096253 A1 | 5/2003 | Nelson et al. |
| 2003/0190647 A1 | 10/2003 | Odera |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0224319 A1 | 11/2004 | Sood et al. |

FOREIGN PATENT DOCUMENTS

| WO | WO91/06678 | 5/1991 |
| WO | WO96/27025 | 9/1996 |
| WO | WO99/05315 | 2/1999 |
| WO | 2006/125267 | * 11/2006 |

OTHER PUBLICATIONS

Eid, et al., Real-Time DNA Sequencing from Single Polymerase Molecules, Science 323:133-138 (Jan. 2, 2009).
Levene, et al., "Zero-Waveguides for Single Molecule Analysis at High Concentrations", Science 299 (5607): 682-686 (2003).
Wilson, D. M., et al. (1997), "Abasic site binding by the human apurinic endonuclease, Ape, and determination of the DNA contact sites, "Nucleic Acids Research 25(5):933-939.
Male, R., et al. (1982) "Polyamine-induce hydrolysis of apurinic sites in DNA and Nucleosomes," Nucleic Acids Research 10(20):6305-6318.

* cited by examiner

*Primary Examiner* — Kenneth R. Horlick
(74) *Attorney, Agent, or Firm* — Deana A. Arnold (57) ABSTRACT

The present invention provides compositions and methods for reducing steric hindrance in the product of nucleic acid polymerase reaction. Methods and compositions of the invention encompass application of exonucleases, endonucleases, and uracil-DNA glycosylases to a nucleic acid polymerase reaction such that newly formed nucleic acid strands are modified (e.g., cleaved) while the polymerase reaction continues to proceed.

23 Claims, 4 Drawing Sheets

PREVENTION AND ALLEVIATION OF STERIC HINDRANCE DURING SINGLE MOLECULE NUCLEIC ACID SYNTHESIS BY A POLYMERASE

CROSS-REFERENCE TO RELATED APPLICATIONS

This application claims the benefit of U.S. Provisional Application No. 61/086,404, filed Aug. 5, 2008, the disclosure of which is incorporated herein by reference in its entirety for all purposes.

FIELD OF THE INVENTION

The present invention is generally related to the Field of molecular biology. The present invention provides compositions and methods for reducing steric hindrance caused by the product of a nucleic acid polymerase reaction. Methods and compositions of the invention encompass but are not limited to application of exonucleases, endonucleases, and glycosylases to the product of a nucleic acid polymerase reaction such that newly formed nucleic acid strands or the portions of the template to which they are annealed are modified while the polymerase reaction continues to proceed along the template nucleic acid.

BACKGROUND OF THE INVENTION

During nucleic acid polymerase reactions, as the polymerase enzyme proceeds along the template, a nascent nucleic acid strand is generated. When such polymerase reactions are conducted in restrictive volumes (i.e., less than 1 µl), steric hindrance problems can arise as the nascent strand grows in length. In restricted volume reactions, the nascent strand is more likely to hinder the progress of the polymerase enzyme than in reactions taking place in less restrictive volumes. Methods for mitigating such steric hindrance would be beneficial in certain polymerase reactions, e.g., those carried out in restrictive volumes.

SUMMARY OF THE INVENTION

The present invention provides methods and compositions for preventing and/or alleviating steric hindrance that may be caused by the product of a nucleic acid polymerase reaction. For example, one strategy for reducing the steric hindrance posed by the nascent strand is to remove or cleave the nascent strand while keeping the template nucleic acid intact.

In certain aspects, the present invention provides methods for reducing steric hindrance resulting from a product of a nucleic acid polymerase reaction. For example, one such method includes the step of conducting the nucleic acid polymerase reaction in the presence of an exonuclease. In certain embodiments of the invention, the nucleic acid polymerase reaction includes a template nucleic acid molecule, and the exonuclease cleaves the product of the reaction, e.g., the nascent nucleic acid strand, but does not cleave the template nucleic acid molecule. In certain related embodiments, the exonuclease is only able to initiate at the 5' end of a single-stranded nucleic acid, e.g., the product of a "rolling-circle" replication reaction in which a circular nucleic acid serves as the template. Certain preferred exonucleases for use with the instant invention include RecJ, lambda exonuclease, and T7 exonuclease. In certain preferred embodiments, the polymerase reaction is conducted in a volume of less than one attoliter.

In another embodiment of the present invention, a method for reducing steric hindrance resulting from a product of a nucleic acid polymerase reaction includes the step of conducting the nucleic acid polymerase reaction in the presence of a restriction endonuclease. In this embodiment, the nucleic acid polymerase reaction includes a template nucleic acid molecule, and the restriction endonuclease cleaves the product of the nucleic acid polymerase reaction but does not cleave the template nucleic acid molecule. In certain preferred embodiments, the restriction enzyme has a four-base-pair recognition site. In further preferred embodiments, the polymerase reaction is conducted in a volume of less than one attoliter.

In another embodiment of the present invention, a method for reducing steric hindrance in the product of a nucleic acid polymerase reaction includes the step of conducting the nucleic acid polymerase reaction in the presence of a uracil-DNA glycosylase enzyme. In this embodiment, the nucleic acid polymerase reaction includes a template nucleic acid molecule, and the uracil-DNA glycosylase removes uracil nitrogenous bases from the product of the nucleic acid polymerase reaction but does not remove nitrogenous bases from the template nucleic acid molecule. In certain preferred embodiments, the polymerase reaction is conducted in a volume of less than one attoliter.

In certain aspects, the invention provides methods of determining a nucleotide sequence of a template nucleic acid molecule. In certain embodiments, the method includes the step of conducting a nucleic acid polymerase reaction in the presence of a set of detectable terminal-phosphate-labeled nucleotides and an exonuclease. In this method, the nucleic acid polymerase reaction results in the addition of the members of the set of detectable terminal-phosphate-labeled nucleotides to a nascent nucleic acid strand and also results in production of a labeled polyphosphates that are released from the members of the set of detectable terminal-phosphate-labeled nucleotides. This method further includes the step of sequentially detecting either the released labeled polyphosphates or the terminal-phosphate-labeled nucleotides that yield the labeled polyphosphates during the polymerase reaction, and subsequent identification of the same. Identification of the released labeled polyphosphates or the terminal-phosphate-labeled nucleotides that yield the labeled polyphosphates determines the nucleotide sequence of the template nucleic acid. In certain embodiments of the invention, the exonuclease cleaves the nascent nucleic acid strand but does not cleave the template nucleic acid.

In another embodiment, the invention provides a method of determining a nucleotide sequence of a template nucleic acid that includes the step of conducting a nucleic acid polymerase reaction in the presence of a set of detectable terminal-phosphate-labeled nucleotides and a restriction endonuclease. In this method, the nucleic acid polymerase reaction results in the addition of detectable terminal-phosphate-labeled nucleotides to a nascent nucleic acid strand and also results in production of labeled polyphosphates that are released from the detectable terminal-phosphate-labeled nucleotides. This method further includes the step of sequentially detecting during the polymerase reaction either the released labeled polyphosphates or the terminal-phosphate-labeled nucleotides that yield the labeled polyphosphates, and subsequent identification of the same. Identification of the released labeled polyphosphates or the terminal-phosphate-labeled nucleotides that yield the labeled polyphosphates determines the nucleotide sequence of the template nucleic acid. In certain embodiments of the invention, the restriction endonuclease cleaves a product of the nucleic acid polymerase reaction but does not cleave the template nucleic acid.

In another embodiment, the invention provides a method of determining a nucleotide sequence of a template nucleic acid that includes the step of conducting a nucleic acid polymerase reaction in the presence of a set of detectable terminal-phosphate-labeled nucleotides, dUTP (or an analog or derivative thereof), and a uracil-DNA glycosylase enzyme. In certain preferred embodiments, the dUTP (or analog or derivative thereof) is a dUTP analog comprising at least four, five, six, seven, or eight phosphate groups. In this method, the nucleic acid polymerase reaction results in the addition of the detectable terminal-phosphate-labeled nucleotides to a nascent nucleic acid strand and also results in production of labeled polyphosphates that are released from the detectable terminal-phosphate-labeled nucleotides. This method further includes the step of sequentially detecting during the polymerase reaction either the released labeled polyphosphates or the terminal-phosphate-labeled nucleotides that yield the labeled polyphosphates, and subsequent identification of the same. Identification of the released labeled polyphosphates or the terminal-phosphate-labeled nucleotides that yield the labeled polyphosphates determines the nucleotide sequence of the template nucleic acid. In certain embodiments of the invention, the uracil-DNA glycosylase removes uracil nitrogenous bases from a product of the nucleic acid polymerase reaction, but does not remove nitrogenous bases from the template nucleic acid. Further, the removal of uracil nitrogenous bases enhances flexibility of the nascent strand, and further increases the likelihood of hydrolytic cleavage of the phosphate backbone of the nascent strand at the resulting abasic sites. In certain embodiments, the method further comprises hydrolysis of abasic sites created by removal of uracil residues from the nascent nucleic acid strand by the uracil-DNA glycosylase. Optionally, the method can be performed in the presence of at least one polyamine or AP endonuclease. Additionally, the set of detectable terminal-phosphate-labeled nucleotides can optionally include terminal-phosphate-labeled thymine-containing nucleotides.

In certain aspects, the invention provides a template nucleic acid that comprises a modification such that an exonuclease, restriction endonuclease, and/or a uracil-DNA glycosylase is unable to cleave the template nucleic acid. Such modifications include but are not limited to non-natural nucleotides at one or both termini of the template nucleic acid, methylation of the template nucleic acid, a protecting group at one or both termini of the template nucleic acid (e.g., a removable protection group), a chemically-modified oligonucleotide extension ligated to an end of the template nucleic acid, as described elsewhere herein. For example, single-stranded template nucleic acid can be protected by a phosphorothioate bond. In certain embodiments, the template nucleic acid is immobilized within an optical confinement, e.g., a zero mode waveguide.

In certain aspects, the invention provides a composition that includes a nucleic acid polymerase, a restriction endonuclease or an exonuclease or a uracil-DNA glycosylase, and a template nucleic acid. In a further aspect, the composition also includes a substrate. In a still further aspect, the nucleic acid polymerase is immobilized on the surface of the substrate. In a still further aspect, the substrate is part of a constricted volume reaction vessel.

In another aspect, the invention provides a kit. Such a kit can include a substrate, which includes a surface. The kit can also include a nucleic acid polymerase. In one aspect, the nucleic acid polymerase is immobilized on the surface of the substrate. In a further aspect, the substrate is part of a constricted volume reaction vessel. Such a kit can also include a restriction endonuclease, an exonucleases, or uracil-DNA glycosylases.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. It will be apparent to one of skill in the art that these additional features are also encompassed by the present invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry and organic synthesis described below are those well known and commonly employed in the art. Standard techniques, or modifications thereof, are used for chemical syntheses and chemical analyses.

Overview

The present invention provides methods and compositions for preventing steric hindrance of a nucleic acid polymerase reaction by the product of that same reaction. In certain embodiments, steric hindrance is prevented or alleviated by cleaving the product of a polymerase reaction. In polymerase reactions, particularly reactions taking place in small volumes, the growing nascent strand can interfere with the activity of the polymerase enzyme as the reaction progresses. The present invention encompasses methods and compositions for modifying (e.g., cleaving, fragmenting, or removing nitrogenous bases from) the product of a nucleic acid polymerase reaction without modifying the template nucleic acid.

The term "template nucleic acid" as used herein is a nucleic acid molecule that serves as a pattern for synthesis of a macromolecule, such as DNA or RNA. For example, during a polymerization reaction, a polymerase enzyme can use the sequence of the template to direct the sequence of nucleotides (or analogs or derivatives thereof) incorporated into a nascent strand, thereby creating a nascent stand that is complementary to the template nucleic acid. The product of a nucleic acid reaction includes the nascent nucleic acid strand that is generated by the polymerase enzyme. The product of a nucleic acid reaction can also include the double-stranded molecule comprising the nascent strand annealed to the complementary region of the template nucleic acid upon which it was synthesized. The present invention also includes methods and compositions for protecting the template nucleic acid from being modified by any enzymes or other molecules applied to reduce steric hindrance posed by the product of the nucleic acid polymerase reaction.

Nucleic Acid Polymerase Reactions

In accordance with the present invention, the compositions and methods described herein can be used to reduce steric hindrance of nucleic acid polymerase reactions. Such steric hindrance may arise from the product of those reactions, in particular in highly processive polymerase reactions that produce long single-stranded or double-stranded nucleic acid products. The growing nascent strand can, in certain embodiments, be thousands of bases in length. For example, some polymerase reactions comprise a circular single-stranded nucleic acid template that is repeatedly processed by a polymerase in a "rolling-circle replication" reaction. The nascent strand produced comprises multiple copies of the complement of the template strand that are displaced by the translocating polymerase enzyme to produce a long concatemer molecule that typically remains attached to the polymerase complex. Certain of the inhibitory effects of having a long nascent strand in a rolling-circle replication embodiment are related to its residence on a circular template, necessitating continuous strand displacement by the polymerase during ongoing synthesis of the nascent strand. Further, certain polymerase reactions comprise a long single-stranded nucleic acid template and form a long double-stranded product through synthesis of the complementary nascent strand on the template. Since double-stranded DNA is a much more rigid structure than single-stranded DNA, the reduced flexibility of the long double-stranded product relative to the initial single-stranded template can cause escalating steric hindrance of the polymerase reaction as the length of the duplex product increases, in addition to steric hindrances that can interfere with the ongoing polymerase reaction, a long single-stranded or double-stranded product attached to a polymerase complex immobilized on a surface can stress the attachment between the surface and the complex (e.g., via the polymerase enzyme or the template nucleic acid), possibly causing displacement of the complex from the surface. In certain embodiments, such displacement effectively ends analysis of the reaction by allowing the complex to move away from the substrate and preventing further monitoring of the reaction by the practitioner. One of ordinary skill will recognize additional negative impacts of having a long polymerase reaction product present in an ongoing polymerase reaction, including but not limited to the possibility that the product may be a substrate for a competing reaction that could confound the ability to monitor the polymerase reaction. As such, an object of the instant invention is to facilitate modification or removal of a polymerase reaction product during the course of the polymerase reaction, i.e., during ongoing incorporation of nucleotides into a growing nascent strand by a polymerase enzyme.

Steric hindrance can be particularly problematic when the nucleic acid polymerase reactions take place in small volumes. The term "small volumes" as used herein refers to volumes of less than about 1 attoliter (al). In an exemplary aspect, the small volume reactions according to the invention are in the range of about 100 zeptoliters (zl) to about 1 al. In another exemplary aspect, the small volume reactions according to the invention are about 50, 100, 150, 200, 250, 300, 350, 400, 450, and 500 zl. In still another exemplary aspect, the small volume reactions according to the invention are in the range of about 20 to about 1000, about 50 to about 750, about 100 to about 500, about 150 to about 450, about 200 to about 400, and about 250 to about 350 zl.

In certain embodiments, the small volumes do not refer to the volume of an entire reaction mixture, but rather refer to a portion of the reaction mixture located within a restricted volume reaction vessel (e.g., a well, optical confinement, microfluidic channel, or other structure within which a reaction is occurring). For example, a reaction volume may comprise a plurality of "small volume reactions," each of which is located within a restricted volume reaction vessel, e.g., in an array of restricted volume reaction vessels on a substrate. Certain preferred embodiments of arrays of restricted volume reaction vessels on a substrate and methods of use and manufacture thereof are further described, e.g., in U.S. Pat. Nos. 7,313,308 and 7,486,865; and U.S. patent application Ser. No. 11/978,138, filed Oct. 26, 2007, and Ser. No. 11/704,733, filed Feb. 9, 2007. As such, the small volume reactions according to the invention are, in an exemplary embodiment, contained in a constricted volume reaction vessel, such as, in one non-limiting example, a zero mode waveguide. Constricted volume reaction vessels, including zero mode waveguides, are known in the art and described further herein. In certain preferred embodiments, a single restricted volume reaction vessel contains a single polymerase reaction, as further described below.

In accordance with the invention, "small volume" nucleic acid polymerase reactions may also be defined in terms of the size of the nucleic acid strands that are part of such reactions. Such nucleic acid strands may be the template nucleic acid or the nascent nucleic acid. In one exemplary embodiment, the small volume reaction may comprise a nucleic acid strand of about 500, 750, 1000, 1250, 1500, 1750, 2000, 2500, 5000, 7500, 10,000, 15,000, 20,000, 50,000, 75,000, and 100,000 bases. The small volume reaction may in another exemplary embodiment comprise a nucleic acid strand of about 500 to about 100,000, of about 1000 to about 50,000, of about 2000 to about 25,000, of about 3000 to about 20,000, of about 4000 to about 15,000, and of about 5000 to about 10,000 bases. In some embodiments, the nascent strand is longer than the template nucleic acid strand, e.g., and may comprise multiple copies of the complement of the template nucleic acid strand. The volume of the small volume reaction defined by the size of the nucleic acid strands may be based on the relaxed sizes of these strands or on the coiled or supercoiled sizes of these strands. As discussed further herein, such nucleic acid strands may be single- or double-stranded, circular or linear.

A nucleic acid polymerase is any of various enzymes, such as DNA polymerase, RNA polymerase, or reverse transcriptase, that catalyze the formation of polynucleotides of DNA or RNA using an existing strand of DNA or RNA as a template. As such, nucleic acid polymerase reactions of the invention may include polymerase enzymes such as DNA polymerases, i.e., Taq polymerases, *E. coli* DNA polymerase I, Klenow fragment, reverse transcriptases, Φ29 related polymerases including wild type Φ29 polymerase and derivatives of such polymerases, T7 DNA polymerase, T5 DNA polymerase, RNA polymerases, and the like. Further descriptions of polymerases are provided in U.S. patent application Ser. No. 11/645,125, filed Dec. 21, 2006; Ser. No. 11/978,210, filed Oct. 26, 2007; Ser. No. 12/384,112, filed Mar. 30, 2009; Ser. No. 12/384,110, filed Mar. 30, 2009; and 61/094,843, filed Sep. 5, 2008; and U.S. Patent Publication Nos. 20070196846 and 20080108082; the disclosures of which are incorporated herein by reference in their entireties for all purposes.

As used herein, the term "polynucleotide" is used interchangeably with "nucleic acid" to mean DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety. Template nucleic acid molecules used in accordance with the invention may be single-stranded or double-stranded, and may be linear or circular molecules.

The methods of the present invention are particularly useful in reducing the steric hindrance that may occur during "sequence-by-incorporation" reactions in which the sequence of bases in a nucleic acid is identified based upon the template-dependent incorporation of complementary nucleotides by a polymerase enzyme. The term "nucleotides" as used herein includes native ribonucleotides and deoxyribonucleotides, as well as analogs, derivatives, mimetics, and any chemical modifications thereof, as further described above. In certain preferred embodiments, nucleotides comprise a detectable label that is indicative of the base composition of the nucleotide such that a signal emitted from the label identifies the base present in the nucleotide. As such, multiple types of differentially labeled nucleotides can be present in a sequencing reaction, and detection and identification of signals emitted from nucleotides incorporated into a nascent strand allows determination of the base sequence of the nascent strand and, by complementarity, the base sequence of the template nucleic acid. In certain preferred embodiments, a label is attached to a nucleotide at a phosphate group that is removed from the nucleotide upon incorporation into the nascent strand, e.g., at a terminal phosphate.

In certain aspects, polymerase reactions are monitored in real time, e.g., during processive incorporation of nucleotides (or analogs thereof) into a nascent strand. For example, in certain embodiments, polymerase reactions of the invention are employed in a single-molecule, real-time sequence-by-incorporation process, e.g., as described in U.S. Pat. Nos. 6,753,200, 7,033,764, 7,056,661, and 7,056,676 and Levene et al., Science 299:682-686, January 2003 *Zero-Mode Waveguides for Single-Molecule Analysis at High Concentration*, the full disclosures of each of which are hereby incorporated herein by reference in their entireties for all purposes, and in particular for their teachings regarding polymerase reactions employed in sequence-by-incorporation processes. Briefly, a polymerase/template/primer complex is provided immobilized upon a surface of a substrate, and the complex is exposed to a complete set of four nucleotides or nucleotide analogs. The analogs are labeled such that incorporation of each nucleotide into the extending primer releases the label from the nucleotide. Preferred nucleotide and nucleotide analogs are described in e.g., the above-incorporated patents, and U.S. Pat. Nos. 7,041,812 and 7,052,839, the full disclosures of which are incorporated herein by reference in their entireties for all purposes and in particular for their teachings regarding such nucleotides and nucleotide analogs and their use in sequencing-by-incorporation methods.

In an exemplary embodiment, the polymerase reaction is isolated within an extremely small observation volume that effectively results in observation of individual polymerase molecules. As a result, an incorporation event provides observation of an incorporating nucleotide analog that is readily distinguishable from non-incorporated nucleotide analogs. In a further exemplary embodiment, such small observation volumes are provided by immobilizing the polymerase enzyme within an optical confinement, such as a Zero Mode Waveguide ("ZMW"). For a description of ZMWs and their application in single molecule analyses, and particularly nucleic acid sequencing, see, e.g., Published U.S. Patent Application No. 2003/0044781, and U.S. Pat. No. 6,917,726, each of which is incorporated herein by reference in its entirety for all purposes, and in particular for its teachings regarding ZMWs. Such sequential reaction and monitoring permits a real-time monitoring of the polymerization reaction and determination of the sequence of the template nucleic acid.

Figure 1:
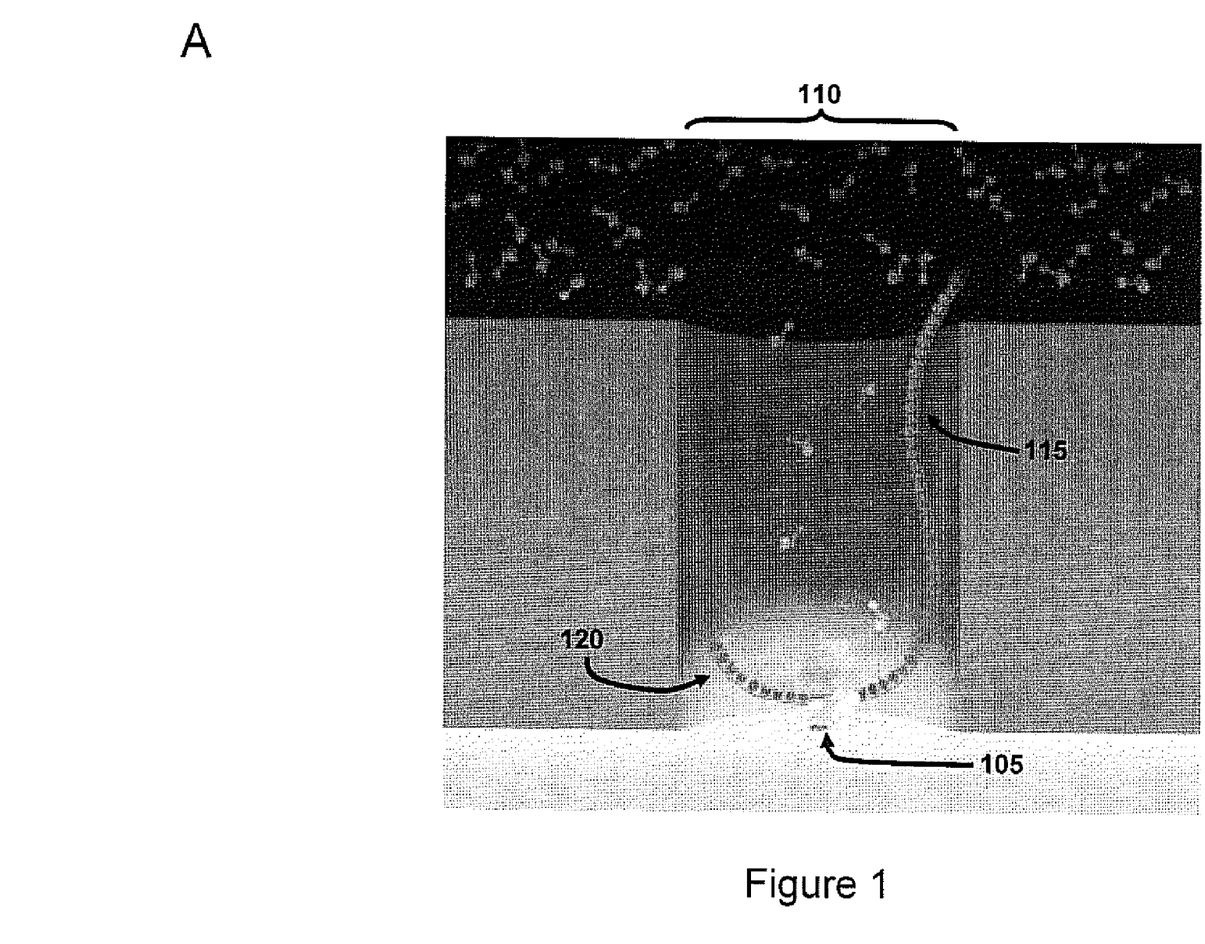
FIG. 1 provides an illustrative example of a single molecule synthesis reaction located within a restricted volume reaction vessel.

FIG. 1 provides an illustrative example of a polymerase 105 immobilized within a zero mode waveguide 110 during conversion of a single-stranded template 115 into a double-stranded product 120. The small volume of the reaction refers to the volume of the zero mode waveguide in which the reaction is immobilized, but the volume of the entire reaction mixture further comprises the volume of the reaction mixture outside the zero mode waveguide.

In further exemplary embodiments, nucleic acid polymerase reactions of the invention include polymerase chain reactions (PCR), transcription, reverse transcription, nucleic acid sequence-based amplification (NASBA), self-sustained sequence replication (3SR), strand displacement amplification (SDA), and branched DNA signal amplification (bDNA) reactions.

Reduction of Steric Hindrance in Nucleic Acid Polymerase Reactions

As a nucleic acid polymerase reaction proceeds, the resultant growing nascent nucleic acid strand can interfere with the progression of the polymerase enzyme—this interference is also referred to herein as "steric hindrance." Such steric hindrance can be especially problematic in small volume reactions, because the growing nascent strand is more likely to encounter and hinder the polymerase enzyme than would be the case in reactions taking place in larger volumes. The present invention provides methods and compositions for reducing and/or preventing the steric hindrance that can be caused by the product of a nucleic acid polymerase reaction. In certain embodiments, steric hindrance is reduced or prevented by cleaving and/or removing at least one or more portions of the growing nascent strand, e.g., by cleavage of the sugar-phosphate backbone or by removal of a base to create an abasic site, which enhances flexibility and is more susceptible to hydrolysis than an unaltered nucleotide. As such, in preferred embodiments the nascent strand produced by a polymerase during a polymerase reaction is rendered unsuitable for use as a single template in a subsequent polymerase reaction, e.g., due to fragmentation and/or other modification.

Using Exonucleases

In certain aspects, the present invention provides methods and compositions for reducing steric hindrance caused by the product of a nucleic acid polymerase reaction by cleaving that product using an exonuclease. An exonuclease is any of various enzymes that cleave nucleotides sequentially from free ends of a nucleic acid substrate. In one exemplary embodiment, a single-stranded nascent nucleic acid produced in nucleic acid polymerase reaction is cleaved or "degraded" with an exonuclease, e.g., a 5'→3' ssDNA exonuclease. In another aspect, a double-stranded molecule comprising the nascent nucleic acid strand annealed to its complementary region on the template nucleic acid is cleaved with an exonuclease, e.g., a dsDNA exonuclease possessing 5'→3' exonucleases activity, 3'→5' exonucleases activity, or both.

In certain embodiments, the exonuclease cleaves the product of the nucleic acid polymerase reaction without cleaving the template nucleic acid. For example, the exonucleases may degrade a single-stranded product produced by strand-displacement of the nascent strand from a circular template. In other cases, the cleavage may occur while the nascent strand is still bound to the template strand, but may be specific for the nascent strand, e.g., due to the polarity of the exonucleases activity. In other embodiments, the exonuclease cleaves the template nucleic acid, but only in regions that have already been used by the polymerase enzyme in the nucleic acid synthesis reaction.

Various exonucleases can be used in accordance with the present invention. Such exonucleases are well known in the art. Exemplary exonucleases for use in the present invention include without limitation: RecJ, lambda exonuclease, T7 exonuclease, exonuclease I, exonuclease III, exonuclease T, and the like. A single type of exonuclease may be utilized according to the invention, or a combination of two or more exonucleases may be used. Certain preferred exonucleases degrade only one strand of a double-strand DNA in the 5' to 3' direction.

In accordance with the invention, the exonuclease may be used simultaneously with a nucleic acid polymerase in a polymerase reaction, such that new nucleotides are being added to the 3' end of the nascent nucleic acid strand by the polymerase enzyme while, at the same time, nucleotides are being removed from the 5' end of the same nascent nucleic acid strand by the exonuclease. In certain embodiments, the exonuclease initiates at only the 5' end of the nascent nucleic acid strand. In another embodiment initiates at only the 3' end of the template nucleic acid strand. In still another embodiment, the exonuclease is able to initiate at either the 3' end of the template strand or 5' end of the nascent nucleic acid strand. In still further embodiments, the exonuclease cleaves both strands of a double-stranded product comprising both the nascent strand and the template strand. In one exemplary embodiment, an exonuclease is present in the reaction mixture at the start of a nucleic acid polymerase reaction of the invention. In another exemplary embodiment, an exonuclease is introduced after initiation of the nucleic acid polymerase reaction, e.g., after the reaction has proceeded for a period of time.

In certain preferred embodiments, exonucleases can be used during sequencing reactions, such as sequencing-by-incorporation reactions, to reduce and/or prevent steric hindrance of polymerase enzyme activity by the growing nascent strand. Such sequencing-by-incorporation reactions are well known in the art and described further herein. In one exemplary embodiment, a sequencing reaction in accordance with the present invention will include the step of conducting a nucleic acid polymerase reaction in the presence of at least one detectable terminal-phosphate-labeled nucleotide and at least one exonuclease. In such an embodiment, the sequencing reaction results in addition of the detectable terminal-phosphate-labeled nucleotide to a nascent nucleic acid strand. In a further embodiment, the reaction also results in production of a labeled polyphosphate that is released from the detectable terminal-phosphate-labeled nucleotide, in this embodiment, the released labeled polyphosphate or the terminal-phosphate-labeled nucleotide are detected and can be identified, and this identification can allow determination of the nucleotide sequence of the template nucleic acid. In certain embodiments, such as those in which a template is repeatedly processed by the polymerase to produce one or more nascent strands comprising one or more copies of the complement of the template, the exonuclease included in the reaction preferably cleaves the nascent nucleic acid strand but does not cleave the template nucleic acid.

Figure 2:
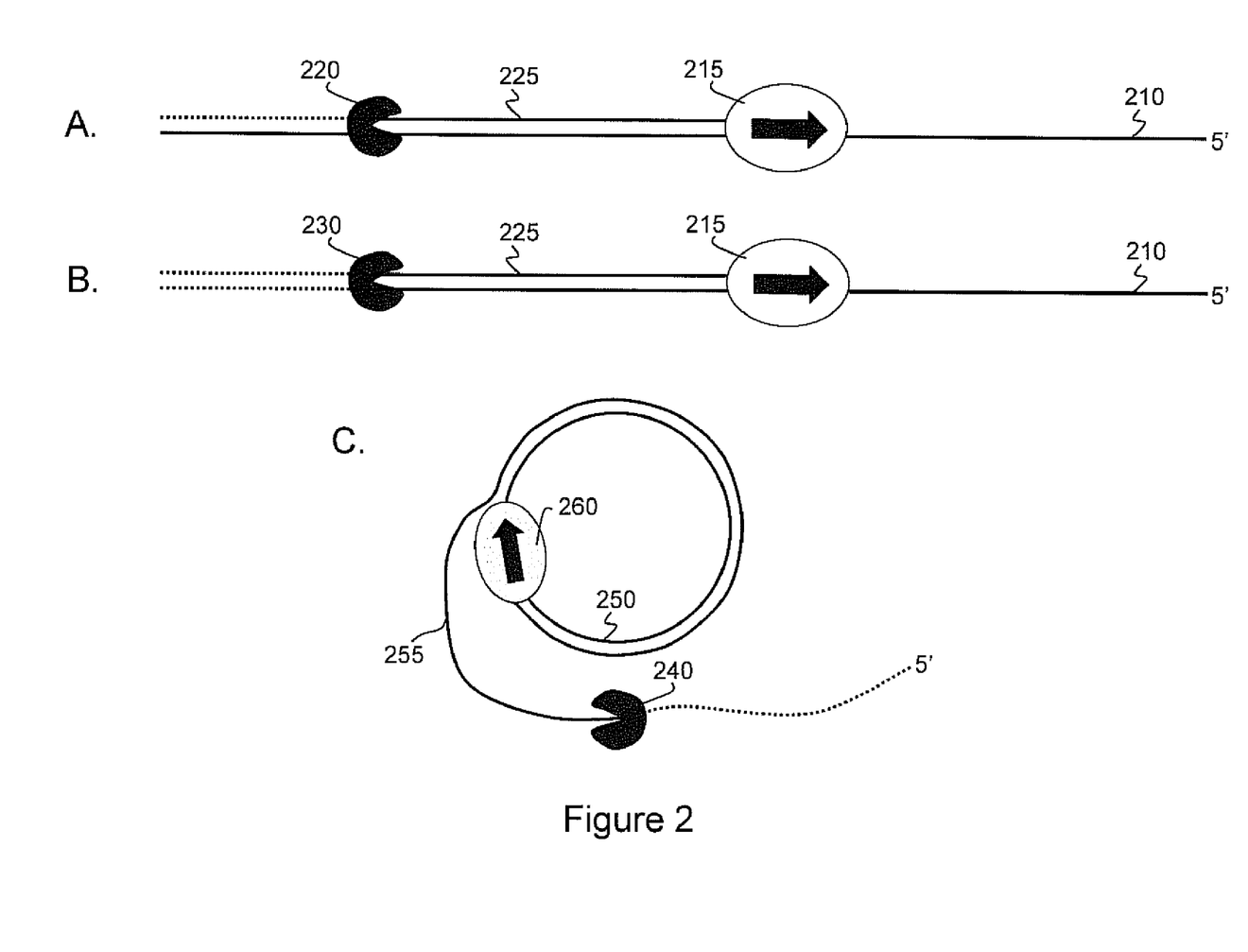
FIG. 2 illustrates certain embodiments of the invention in which an exonuclease acts upon a product of a single molecule synthesis reaction. Embodiments comprising a dsDNA-dependent ssDNA exonuclease, a dsDNA exonuclease, and a ssDNA-dependent ssDNA exonuclease are shown in A, B, and C, respectively.

FIG. 2 provides exemplary embodiments of certain single molecule synthesis reactions comprising an exonuclease. The diagram in FIG. 2A illustrates a polymerase enzyme 215 processing a linear, single-stranded template 210, thereby synthesizing a complementary nascent strand 225. A dsDNA exonuclease 220 possessing 5'→3' exonuclease activity degrades the nascent strand from the 3' terminus during synthesis of the 5' terminus of the nascent strand by the polymerase 215. Although a 5'→3' dsDNA exonuclease is shown, optionally a 3'→5' exonucleases could be used, e.g., in applications in which preservation of the template nucleic acid is not necessary or desired. FIG. 2B also depicts a polymerase enzyme 215 processing a linear, single-stranded template 210 and synthesizing a complementary nascent strand 225. However, the dsDNA exonuclease 230 possesses both 5'→3' and 3'→5'exonuclease activity that degrades both the nascent strand and the template strand during nascent strand synthesis by the polymerase 215. FIG. 2C illustrates a polymerase enzyme 260 that possesses strand displacement activity processing a circular, single stranded template 250 to synthesize a concatemeric single-stranded nascent strand 255. A ssDNA exonucleases 240 degrades the nascent strand from the 3' terminus after it has been displaced by the translocating polymerase 260. In each embodiment depicted in FIG. 2, steric hindrance in a polymerase reaction is alleviated by cleavage of the product of the polymerase reaction by an exonuclease.

Using Restriction Endonucleases

In certain aspects, the invention provides methods and compositions for reducing steric hindrance caused by the product of a nucleic acid polymerase reaction by utilizing one or more restriction endonucleases to cleave that product. In certain exemplary embodiments, the nascent nucleic acid strand produced in the nucleic acid polymerase reaction is cleaved with a restriction endonuclease. In other embodiments, the double-stranded nucleic acid molecule comprising the nascent nucleic acid strand annealed to the complementary region on the template nucleic acid upon which it was synthesized is cleaved with a restriction endonuclease. In a further aspect, the restriction endonuclease cleaves the product of the nucleic acid polymerase reaction, but only in regions of the template nucleic acid that have already been used by the polymerase enzyme to add a nucleotide to the growing nascent strand in a template-dependent manner.

A restriction endonuclease is any of a group of enzymes that catalyzes the cleavage of DNA molecules in a sequence-specific manner. Various restriction endonucleases can be used in accordance with the present invention. Such restriction endonucleases are well known and characterized in the art. In one exemplary embodiment, restriction endonucleases with four-base-pair recognition sites are used in accordance with the invention. In another non-limiting exemplary embodiment, a restriction endonuclease utilized in accordance with the present invention is selected from a group that includes: AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeI, BamHI, BanI, BanII, BbsI, BbvCI, BbvI, BccI, BceAI, BcgI, BciVI, BelI, BfaI, BfuAI, BglI, BglII, BlpI, Bme1580I, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8II, ClaI, CspCI, CviAII, CviKI-1, CviQI, DdeI, DpnI, DpnII, DraI, DraIII, DrdI, EaeI, EagI, EarI, EciI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy188I, Hpy188III, Hpy99I, HpyCH4III, HpyCH4IV, HpyCH4V, KasI, KpnI, MboI, MboII, MfeI, MluI, MlyI, MmeI, MnlI, MscI, MseI, MslI, MspAII, MspI, MwoI, NaeI, NarI, NciI, NcoI, NdeI, NgoMIV, NheI, NlaIII, NlaIV, NotI, NruI, NsiI, NspI, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, Taq$^\alpha$I, TfiI, TliI, TseI, Tsp45I, Tsp509I, TspMI, TspRI, Tth111I, XbaI, XcmI, XhoI, XmaI, XmnI, and ZraI. A single type of restriction endonuclease may be utilized according to the invention, or a combination of two or more such endonucleases may be used.

In accordance with the invention, restriction endonucleases can be used during sequencing reactions, such as sequencing-by-incorporation reactions, to reduce and/or prevent any steric hindrance of polymerase enzyme activity by the growing nascent strand. Such sequencing-by-incorporation reactions are well known in the art and described further herein. In accordance with the invention, the restriction endonuclease may be used simultaneously with a nucleic acid polymerase in a polymerase reaction, such that new nucleotides are being added to the 3' end of the nascent nucleic acid strand by the polymerase enzyme while, at the same time, cleavage of the same nascent nucleic acid strand is carried out by the restriction endonuclease at one or more positions within a product of the reaction comprising the nascent nucleic acid strand, e.g., that has exited the polymerase complex. In certain embodiments, the restriction endonuclease cleaves only the nascent nucleic acid strand. In other embodiments, the restriction endonuclease cleaves only the template strand when duplexed with the nascent strand. In other embodiments, the restriction endonuclease cleaves both strands of a double-stranded product comprising the nascent strand and the template strand. In one exemplary embodiment, a restriction endonuclease is present in the reaction mixture at the start of a nucleic acid polymerase reaction of the invention. In another exemplary embodiment, a restriction endonuclease is introduced after initiation of the nucleic acid polymerase reaction, e.g., after the reaction has proceeded for a period of time.

In one exemplary aspect, a sequencing reaction in accordance with the present invention will include the step of conducting a nucleic acid polymerase reaction in the presence of at least one detectable terminal-phosphate-labeled nucleotide and at least one restriction endonuclease. In one such embodiment, the sequencing reaction results in addition of the detectable terminal-phosphate-labeled nucleotide to a nascent nucleic acid strand. In a further embodiment, the reaction also results in production of a labeled polyphosphate that is released from the detectable terminal-phosphate-labeied nucleotide. In such an embodiment, the released labeled polyphosphate or the terminal-phosphate-labeled nucleotide can be detected and subsequently identified, and this identification can allow determination of the nucleotide sequence of the template nucleic acid. In certain embodiments, such as those in which a template is repeatedly processed by the polymerase to produce one or more nascent strands comprising one or more copies of the complement of the template, a restriction endonuclease included in the reaction preferably cleaves the product of the polymerase reaction but does not cleave the template nucleic acid.

Figure 3:
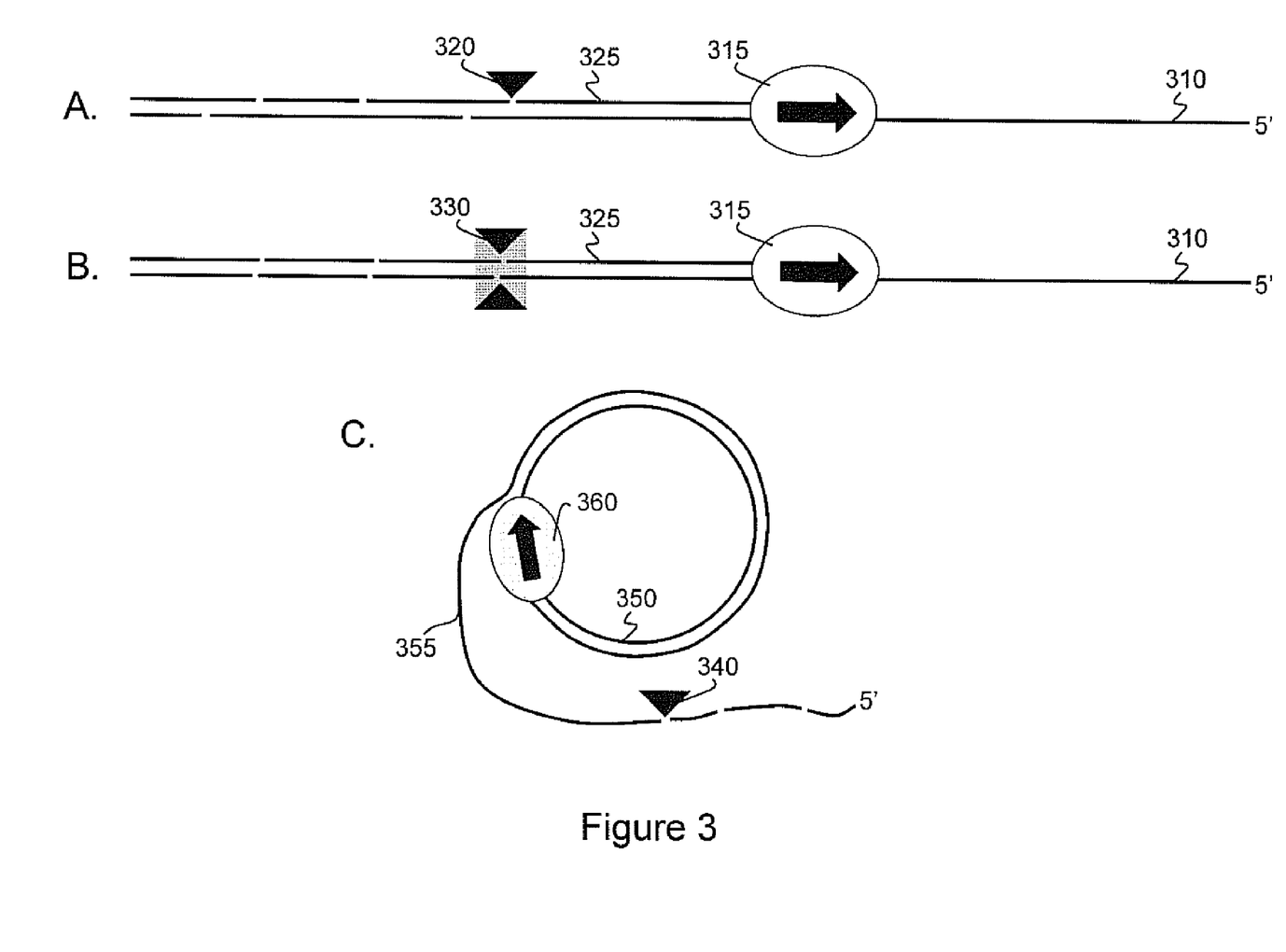
FIG. 3 illustrates certain embodiments of the invention in which an endonuclease acts upon a product of a single molecule synthesis reaction. Embodiments comprising a dsDNA-dependent ssDNA endonuclease, a dsDNA endonuclease, and a ssDNA-dependent ssDNA endonuclease are shown in A, B, and C, respectively.

FIG. 3 provides exemplary embodiments of certain single molecule synthesis reactions comprising an endonuclease. The diagram in FIG. 3A illustrates a polymerase enzyme 315 processing a linear, single-stranded template 310, thereby synthesizing a complementary nascent strand 325. A dsDNA-dependent ssDNA endonuclease 320 cleaves the sugar-phosphate backbone of the nascent strand 325 and the template strand 310 in a sequence-specific manner during synthesis of the nascent strand by the polymerase 315. Although both the template and nascent strand are shown to be susceptible to cleavage by the endonuclease, in some embodiments cleavage is restricted to the nascent strand, e.g., in applications in which preservation of the template nucleic acid is necessary and/or desirable as further described below. FIG. 3B also depicts a polymerase enzyme 315 processing a linear, single-stranded template 310 and synthesizing a complementary nascent strand 325. However, the dsDNA endonuclease 330 cleaves the sugar-phosphate backbone of both the nascent strand and the template strand at or proximal to a recognition site during nascent strand synthesis by the polymerase 315. FIG. 3C illustrates a polymerase enzyme 360 that possesses strand displacement activity processing a circular, single stranded template 350 to synthesize a concatemeric single-stranded nascent strand 355. A ssDNA endonuclease 340 degrades the nascent strand in a sequence-specific manner after it has been displaced by the translocating polymerase 360. Although this rolling-circle synthesis reaction is shown with a ssDNA endonuclease 340, it could also or alternatively include a dsDNA-dependent ssDNA endonuclease. Such an embodiment would preferably include modification of the template strand to protect it from endonucleolytic cleavage, thereby promoting greater processivity of the polymerase enzyme by preservation of the template on which it is translocating. Methods for protecting a template strand from cleavage are further discussed below. In each embodiment depicted in FIG. 3, steric hindrance in a polymerase reaction is alleviated by cleavage of the product of the polymerase reaction by an endonuclease.

Using Uracil-DNA Glycosylases

In one aspect, the present invention provides methods for reducing steric hindrance caused by the product of a nucleic acid polymerase reaction by modifying that product using a uracil-DNA glycosylase. A uracil-DNA glycosylase is any of various enzymes that remove uracil nitrogenous bases from single-stranded or double-stranded DNA without destroying the sugar-phosphate backbone. The resulting abasic sites (also termed "apurinic/apyrimidinic (AP) sites") are susceptible to hydrolytic cleavage, so removal of uracil bases is usually accompanied by fragmentation of the DNA. Further, the introduction of abasic sites adds flexibility to the nascent strand, thereby mitigating steric hindrance to some extent even absent fragmentation. Since uracil-DNA glycosylases can act on single-stranded or double-stranded DNA, uracil residues can be removed from the nascent strand both when bound to the template strand or when rendered single-stranded, e.g., by strand displacement of the nascent strand from the template strand.

In certain embodiments, a nucleic acid that does not comprise dUTP nucleotides is a template in a single-molecule sequencing reaction in the presence of dUTP nucleotides. The dUTP nucleotides can entirely replace dTTP residues in the reaction mixture, or a combination of dUTP and dTTP may be present, as described in more detail below. As a polymerase processes the template, nucleotides comprising uracil nucleobases are incorporated into the nascent strand, but the nucleotide composition of the template strand remains unchanged. This underscores one additional advantage of the methods comprising incorporation and subsequent removal of uracil residues, which is that the template strand need not be modified to be preserved during the course of the reaction. As such, the template can be used multiple times in the same or additional polymerase reactions without any "protective" chemical modifications, which are desired in certain embodiments of the invention comprising nuclease degradation of the nucleic acid product. For example, certain embodiments comprise repeated processing of a template nucleic acid by the polymerase to produce one or more nascent strands comprising one or more copies of the complement of the template. By only modifying the nascent strand, the template strand is preserved for additional nascent strand generation by the same or a different polymerase enzyme.

DNA-uracil glycosylases remove uracil residues from single- and double-stranded DNA without cleavage of the sugar-phosphate backbone. Various uracil-DNA glycosylases can be used in accordance with the present invention. Such uracil-DNA glycosylases are well known in the art. Exemplary uracil-DNA glycosylases for use in the present invention include without limitation: *E. coli* UDG, marine bacterium BMTU 3346 UNG, *Archaeoglobus fulgidus* UDG and *H. sapiens* UNG, all of which are commercially available, e.g., from Roche Applied Science, New England Biolabs, Invitrogen, Affymetrix, and/or Fermentas Life Sciences. A single type of uracil-DNA glycosylase may be utilized according to the invention, or a combination of two or more uracil-DNA glycosylases may be used.

In accordance with the invention, the uracil-DNA glycosylase may be used simultaneously with a nucleic acid polymerase in a polymerase reaction, such that new nucleotides are being added to the 3' end of the nascent nucleic acid strand by the polymerase enzyme while, at the same time, uracils are being removed from the same nascent nucleic acid strand by the uracil-DNA glycosylase. In certain embodiments in which a DNA molecule is the template nucleic acid, the uracil-DNA glycosylase acts only on the nascent nucleic acid strand since a DNA template is typically lacking uracil residues. In one exemplary embodiment, a uracil-DNA glycosylase is present in the reaction mixture at the start of a nucleic acid polymerase reaction of the invention. In another exemplary embodiment, a uracil-DNA glycosylase is introduced after initiation of the nucleic acid polymerase reaction, e.g., after the reaction has proceeded for a period of time.

In certain preferred embodiments, uracil-DNA glycosylases can be used during sequencing reactions, such as sequencing-by-incorporation reactions, to reduce and/or prevent steric hindrance of polymerase enzyme activity by the growing nascent strand. Such sequencing-by-incorporation reactions are well known in the art and described further herein. In one exemplary embodiment, a sequencing reaction in accordance with the present invention will include the step of conducting a nucleic acid polymerase reaction in the presence of at least one detectable terminal-phosphate-labeled nucleotide, dUTP (or an analog or derivative thereof), and at least one uracil-DNA glycosylase. In such an embodiment, the sequencing reaction results in addition of the detectable terminal-phosphate-labeled nucleotide and dUTP into a nascent nucleic acid strand. In a further embodiment, the reaction also results in production of a labeled polyphosphate that is released from the detectable terminal-phosphate-labeled nucleotide. In this embodiment, the released labeled polyphosphate or the terminal-phosphate-labeled nucleotide are detected and can be identified, and this identification can allow determination of the nucleotide sequence of the template nucleic acid. The uracil-DNA glycosylase will act on the double-stranded product of the sequencing reaction that comprises the nascent strand and the template on which it was assembled. Uracil residues in this product are removed by the uracil-DNA glycosylase producing abasic sites. The presence of abasic sites in the double-stranded or single-stranded product increases flexibility, which can ease steric hindrance caused by the elongating product in the restricted volume reaction vessel.

The resulting abasic sites are susceptible to hydrolytic cleavage, which causes fragmentation of the strand comprising the abasic site, e.g., in the nascent strand. The hydrolytic cleavage of the abasic strand can be increased by altering reaction conditions, e.g., by increasing the reaction temperature or by addition of reaction components that promote hydrolysis. For example, an AP endonuclease can be included in the reaction mixture to ensure fragmentation of the strand containing the AP sites. For example, Class II AP endonucleases catalyze the hydrolysis of the 5'-phosphodiester of an abasic site to generate a 3'-OH group and a 5'-abasic residue. (For more information on AP endonucleases, see, e.g., Wilson, et al. (1997) Nuc. Ac. Res. 25 (5):933-939, and Demple, et al. (1994) Annu. Rev. Biochem. 63:915-948, both of which are incorporated by reference herein in their entireties for all purposes.) Further, hydrolysis of apurinic sites in DNA can be induced by polyamines and other amines, such as spermine, spermidine, putrescine, and cadaverine. Further information on polyamine-induced hydrolysis of abasic sites can be found in the art, e.g., Male, et al. (1982) Nuc. Ac. Res. 10 (20):6305-6318; Lindahl, et al. (1972) Biochemistry 11:3618-3623; Tamm, et al. (1952) J. Biol. Chem. 195:40-63; and Tamm, et al. (1952) J. Biol. Chem. 199:313-327, the disclosures of all of which are incorporated herein by reference in their entireties for all purposes.

Figure 4:
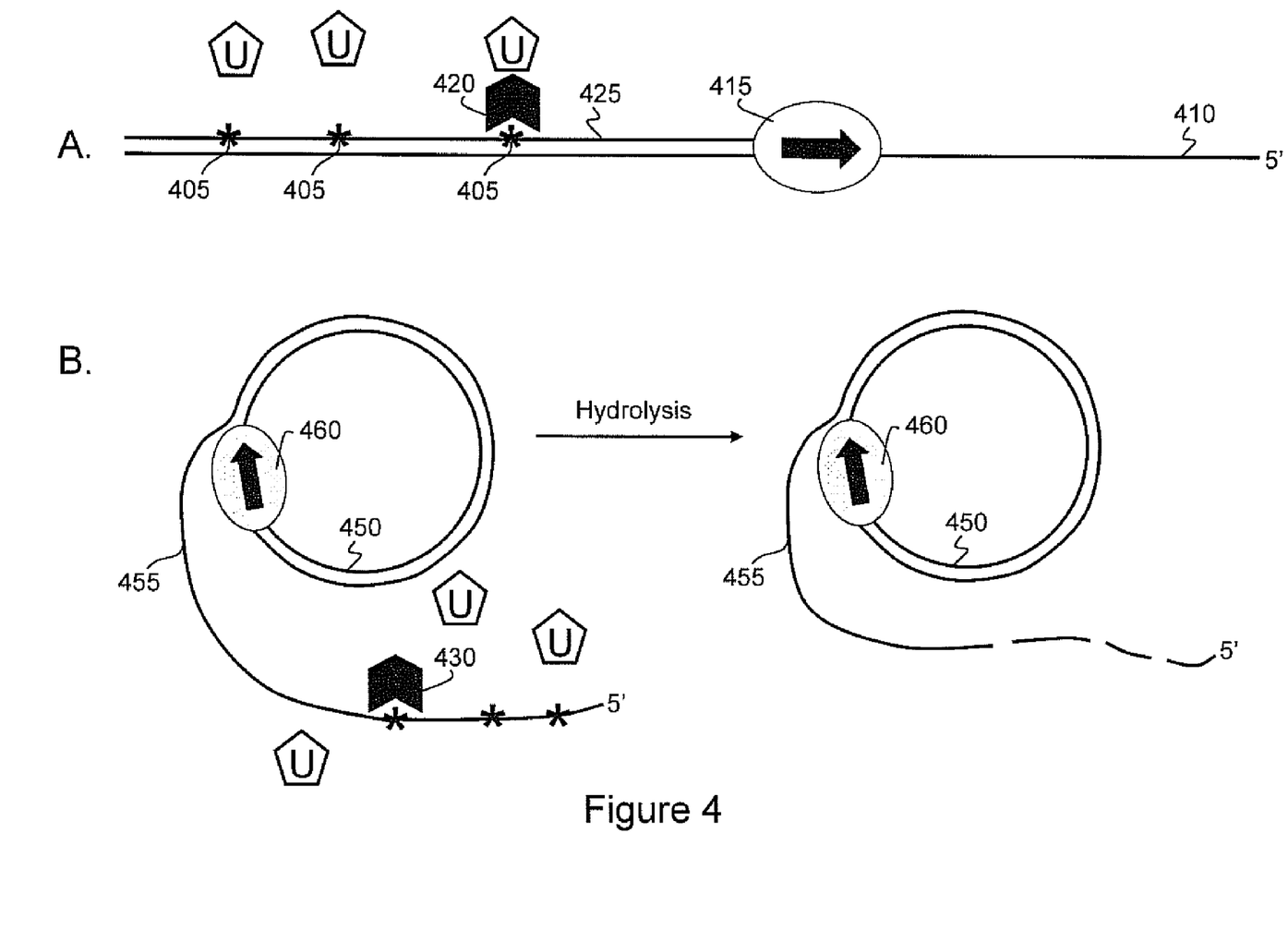
FIG. 4 illustrates certain embodiments of the invention in which a uracil-DNA glycosylase acts upon a product of a single molecule synthesis reaction. Embodiments comprising a linear ssDNA template and a circular ssDNA template are shown in A and B, respectively.

FIG. 4 provides exemplary embodiments of certain single molecule synthesis reactions comprising a uracil-DNA glycosylase. The diagram in FIG. 4A illustrates a polymerase enzyme 415 processing a linear, single-stranded template 410, thereby synthesizing a complementary nascent strand 425. A uracil-DNA glycosylase 420 cleaves the N-glycosylic bond in dUTP to remove the uracil base and generate an abasic (AP) nucleotide (405) in the nascent strand 425 during synthesis of the nascent strand by the polymerase 415. In preferred embodiments, only the nascent strand comprises uracil residues that were incorporated by the polymerase during single-molecule synthesis reaction, and modification by the uracil-DNA glycosylase is therefore restricted to the nascent strand. FIG. 4B illustrates a polymerase enzyme 460 that possesses strand displacement activity processing a circular, single stranded template 450 to synthesize a concatemeric single-stranded nascent strand 455. A uracil-DNA glycosylase 430 removes uracil residues from the nascent strand 455 after it has been displaced by the translocating polymerase 460. The abasic sites in the nascent strand are susceptible to hydrolysis, after which the nascent strand is fragmented. Methods for promoting hydrolysis of abasic sites are well known in the art and further described elsewhere herein. Although this rolling-circle synthesis reaction is shown with the uracil-DNA glycosylase acting only on the single-stranded portion of the nascent strand, uracil-DNA glycosylases can also act on double-stranded DNA so uracil residues can also be removed from the nascent strand when bound to the template strand. In each embodiment depicted in FIG. 4, steric hindrance in a polymerase reaction is alleviated by modification of the product of the polymerase reaction by a uracil-DNA glycosylase, e.g. by the increased flexibility of a nucleic acid comprising abasic sites and by the higher susceptibility of the nascent strand to fragmentation.

Protection of Template Nucleic Acid

In accordance with the invention, it can be advantageous to protect the template nucleic acid from methods and compositions used to alleviate and/or prevent steric hindrance from the product of a polymerase reaction. Such protection allows the polymerase reaction to continue with the intact template nucleic acid while the product of the polymerase reaction is cleaved and/or removed. For example, a polymerase can continue around a circular template multiple times to generate a long, concatemeric nascent strand comprising multiple copies of the complement of the template strand. Further, an immobilized linear template can be repeatedly processed by the same polymerase, or can be processed by multiple different polymerases, in some embodiments simultaneously. Damage to the template that prevents further processing by a polymerase would prevent such repetitive processing of the template (absent any means to repair the template).

In certain aspects, the template nucleic acid used in nucleic acid polymerase reactions according to the invention is modified such that a restriction endonuclease or exonuclease is unable to cleave the modified template nucleic acid. For example, in certain embodiments template nucleic acids of the invention are modified to comprise at least one non-natural nucleotide at one or both termini. Such non-natural nucleotides are well known in the art and include without limitation: peptide nucleic acids (PNAs), locked nucleic acids (LNA), oligonucleotide N3'→P5' phosphoramidates, oligo-2'-O-alkylribonucleotides, and the like. In other exemplary embodiments, template nucleic acids of the invention are methylated. Such a modification can prevent a restriction endonuclease from cleaving the template nucleic acid.

In still other exemplary embodiments, template nucleic acids of the invention are modified to include a protecting group on at least one nucleotide. Such a protecting group may in some embodiments be a removable protecting group. In further embodiments, such protecting groups comprise a chemically modified oligonucleotide extension ligated to an end of the template nucleic acid. As used herein, a chemically modified oligonucleotide extension comprises a short polymer of nucleotides, wherein one or more of the nucleotides are altered in ways known in the art. For example, such chemically modified oligonucleotide extensions can include phosphorothioate bonds or spacers such as C3, 9, C12 and 18 (Glen Research). 3'-Spacer C3 CPG may act as a blocker of exonuclease activity at the 3'-terminus. In one embodiment, Spacer 18 has a structure according to the formula:

In other exemplary embodiments, template nucleic acids can be protected using a 5'-Aldehyde-Modifier C2 Phosphoramidite (Glen Research) or a 9-fluorenylmethoxycarbonyl (Fmoc) protecting group.

In certain exemplary embodiments, the template nucleic acids are protected with a removable protecting group that is a photoremovable blocking group. Such photoremovable blocking groups can in one exemplary embodiment of the invention be incorporated with a triphosphate nucleotide as the last base unit on the template nucleic acid. Such incorporation can be achieved in one non-limiting example by enzymatically using a DNA polymerase to give the targeted nucleic acid a photoremovable blocking group.

A number of different types of photoremovable chemical blocking groups have been described in the art. In general, such groups include, e.g., nitroveratryl, 1-pyrenylmethyl, 6-nitroveratryloxycarbonyl, dimethyldimethoxybenzyloxycarbonyl, 2-nitrobenzyloxycarbonyl, methyl-6-nitropiperonyloxycarbonyl, 2-oxymethylene anthraquinone, dimethoxybenzyloxy carbonyl, 5-bromo-7-nitroindolinyl, o-hydroxy-alpha-methyl cinnamoyl, and mixtures thereof, the compositions and applications of which are described in, e.g., U.S. Pat. Nos. 5,412,087, 5,143,854, 6,881,836, Albert et al., Nucl. Acids Res. (2003) 31 (7):e35, Beier et al., Nucleic Acids Res. (2000) 28 (4):e11, Pon et al, Nucleic Acids Res.

(2004) 32 (2):623-631, Olejnik et al., Nucleic Acids Res. (1998) 26 (15):3572-3576, and Blanc et al. J. Org. Chem. (2002) 67:5567-5577, each of which is incorporated herein by reference in its entirety for all purposes, and in particular for teachings related to photoremovable chemical blocking groups.

Other methods and compositions for protecting template nucleic acids are well known in the art and can be used in accordance with the present invention.

Compositions of the Invention

In certain aspects, the invention provides a composition that includes a nucleic acid polymerase, a substrate, one or more restriction endonucleases or exonucleases, and a template nucleic acid. In certain exemplary embodiments, one or more of the nucleic acid polymerase, the template nucleic acid and the restriction endonuclease or exonuclease are immobilized on the surface of the substrate. In some embodiments, the substrate comprises one or more zero mode waveguides or other optical confinements. In further embodiments, the template nucleic acid is modified as described further herein such that the restriction endonuclease or exonuclease is unable to cleave the template nucleic acid. In still further embodiments, the composition further includes at least four different nucleotides or nucleotide analogs, and in preferred embodiments, the at least four nucleotides or nucleotide analogs are labeled. For example, one or more of the at least four nucleotides or nucleotide analogs are preferably differentially labeled such that signals detected from each are distinct from one another, and the signal is indicative of the type of nucleotide bearing the label.

In certain aspects, the invention provides a composition that includes a nucleic acid polymerase, a substrate, one or more uracil-DNA glycosylases, and a template nucleic acid. In certain exemplary embodiments, one or more of the nucleic acid polymerase, the template nucleic acid and the one or more uracil-DNA glycosylases are immobilized on the surface of the substrate. In some embodiments, the substrate comprises one or more zero mode waveguides or other optical confinements. In certain embodiments, the composition further includes at least four different nucleotides or nucleotide analogs, wherein at least one is dUTP or a derivative or analog thereof. In preferred embodiments, the at least four nucleotides or nucleotide analogs are labeled. For example, one or more of the at least four nucleotides or nucleotide analogs are preferably differentially labeled such that signals detected from each are distinct from one another, and the signal is indicative of the type of nucleotide bearing the label. In certain embodiments, the composition comprises at least five different nucleotides or nucleotide analogs, wherein at least one is dUTP (which includes derivatives or analogs thereof) and at least one other is dTTP (which includes derivatives or analogs thereof). For example, a composition of the invention can include a ratio of dUTP:dTTP equal to about 20:1, 15:1, 10:1, 7.5:1, 5:1, 4:1, 3:1, 2:1, 1:1, 2:1, 3:1, 4:1, 5:1, 7.5:1, 10:1, 15:1, or 20:1. In other embodiments, the concentration of dUTP may be between 20- and 100-fold higher than the concentration of dTTP, and vice versa. In certain embodiments, a ratio of dUTP:dTTP is selected to ensure sufficient modification of the reaction product to alleviate steric hindrance while allowing efficient nucleotide incorporation into the nascent strand and processive polymerase activity. In certain embodiments, a composition of the invention comprises at least one uracil-DNA glycosylase and at least one polyamine. In other embodiments, a composition of the invention comprises at least one uracil-DNA glycosylase and at least one AP endonuclease. In yet further embodiments, a composition of the invention comprises at least one uracil-DNA glycosylase and a buffer that enhances hydrolysis at abasic sites in the nascent strand.

As will be appreciated, substrates that are part of compositions of the invention can comprise any material capable of supporting one or more molecules of the invention, including nucleic acid polymerases, restriction endonucleases, exonucleases, and template nucleic acids. Exemplary substrate materials include, but are not limited to, inorganic crystals, inorganic glasses, inorganic oxides, metals, organic polymers and combinations thereof. Inorganic glasses and crystals of use in the substrate include, but are not limited to, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, CRYSTAL GROWTH THEORY and TECHNIQUES, Plenum Press, New York 1974. Alternatively, the crystals can be purchased commercially (e.g., Fischer Scientific). Inorganic oxides of use in the present invention include, but are not limited to, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SnO_2$, $PbO_2$ and the like. Metals of use in the substrates of the invention include, but are not limited to, gold, silver, platinum, palladium, nickel, copper and alloys and composites of these metals.

Kits of the Invention

In certain aspects, the present invention provides kits for the prevention of steric hindrance during nucleic acid polymerase reactions. In certain exemplary embodiments, such kits include a substrate, which comprises a surface, a nucleic acid polymerase, and a restriction endonuclease and/or an exonuclease. In further exemplary embodiments, one or more of the restriction endonuclease and/or exonuclease and the nucleic acid polymerase are immobilized on the surface of the substrate. In certain exemplary embodiments, such kits include a substrate, which comprises a surface, a nucleic acid polymerase, and a uracil-DNA glycosylase. In further exemplary embodiments, one or more of the uracil-DNA glycosylase and the nucleic acid polymerase are immobilized on the surface of the substrate. In some embodiments, the kit includes at least four or five nucleotides or nucleotide analogs. In certain preferred embodiments, one or more of the at least four or five nucleotides or nucleotide analogs included in such a kit are labeled. For example, the at least four or five nucleotides or nucleotide analogs are preferably differentially labeled such that signals detected from each are distinct from one another, and the signal is indicative of the type of nucleotide bearing the label.

Kits of the invention may further include any buffers, reagents and co-factors for use in nucleic acid polymerase reactions and/or with exonucleases, restriction endonucleases, and/or uracil-DNA glycosylases used in accordance with the invention. Such buffers, reagents and co-factors are well-known in the art. It will be appreciated that the combination of buffers, reagents and co-factors used in kits of the invention will depend on the nucleic acid polymerases, restriction endonucleases and exonucleases, uracil-DNA glycosylases used in this aspect of the invention.

Kits of the invention may also include one or more reagents for protecting a template nucleic acid from restriction endonuclease and/or exonuclease activity, according to the invention as described further herein. Such reagents are well-known in the art. Kits of the invention may also include one or more reagents for promoting hydrolysis at AP sites in the nascent strand, according to the invention as described further herein.

In certain aspects, the present invention provides methods for alleviating steric hindrance of polymerase reactions, and in particular polymerase reactions confined to a restricted volume reaction vessel. In certain aspects, compositions and kits are provided, e.g., for use in carrying out certain methods of the invention.

It is to be understood that although described in some detail for purposes of illustration it is not intended to be restrictive. It will be readily appreciated to one skilled in the art that a number of variations and modifications known or appreciated by those of skill in the art may be practiced within the scope and spirit of present invention. The scope of the invention should, therefore, be determined not with reference to the above description, but should instead be determined with reference to the appended claims, along with the full scope of equivalents to which such claims are entitled. Unless otherwise clear from the context or expressly stated, any concentration values provided herein are generally given in terms of admixture values or percentages without regard to any conversion that occurs upon or following addition of the particular component of the mixture. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. To the extent not already expressly incorporated herein, all published references and patent documents referred to in this disclosure are incorporated herein by reference in their entireties for all purposes.

We claim:

1. A method for reducing steric hindrance resulting from a product of a nucleic acid polymerase reaction, said method comprising conducting said nucleic acid polymerase reaction in the presence of an enzyme selected from the group consisting of an exonuclease, an endonuclease, and a uracil-DNA glycosylase, wherein said nucleic acid polymerase reaction includes a template nucleic acid, and wherein said enzyme modifies said product but does not modify said template nucleic acid, wherein said enzyme is an exonuclease that is only able to initiate at a 5' end of a single-stranded nucleic acid.

2. The method of claim 1, wherein said exonuclease is selected from the group consisting of RecJ, lambda exonuclease, and T7 exonuclease.

3. A method for reducing steric hindrance resulting from a product of a nucleic acid polymerase reaction, said method comprising conducting said nucleic acid polymerase reaction in the presence of an enzyme selected from the group consisting of an exonuclease, an endonuclease, and a uracil-DNA glycosylase, wherein said nucleic acid polymerase reaction includes a template nucleic acid, and wherein said enzyme modifies said product but does not modify said template nucleic acid, wherein said enzyme is a restriction endonuclease with a four-base-pair recognition site.

4. A method for reducing steric hindrance resulting from a product of a nucleic acid polymerase reaction, said method comprising conducting said nucleic acid polymerase reaction in the presence of an enzyme selected from the group consisting of an exonuclease, an endonuclease, and a uracil-DNA glycosylase, wherein said nucleic acid polymerase reaction includes a template nucleic acid, and wherein said enzyme modifies said product but does not modify said template nucleic acid, wherein the template nucleic acid comprises a modification such that said enzyme is unable to modify said template nucleic acid.

5. The method of claim 4, wherein said modification comprises a non-natural nucleotide at one or more termini of said template nucleic acid.

6. The method of claim 4, wherein said modification comprises methylation of said template nucleic acid.

7. The method of claim 4, wherein said modification comprises a protecting group on at least one nucleotide of said template nucleic acid.

8. The method of claim 4, wherein said modification comprises a chemically modified oligonucleotide extension ligated to an end of said template nucleic acid.

9. The method of claim 8, wherein said chemically modified oligonucleotide extension comprises a phosphorothioate bond or Spacer 18.

10. The method of claim 3, wherein said template nucleic acid is selected from the group consisting of a circular nucleic acid molecule, a double-stranded template nucleic acid, and a single-stranded template nucleic acid.

11. The method of claim 4, wherein said template nucleic acid is selected from the group consisting of a double-stranded template nucleic acid, a single-stranded template nucleic acid, and a circular nucleic acid molecule.

12. The method of claim 1, wherein said template nucleic acid is selected from the group consisting of a single-stranded template nucleic acid, a double-stranded template nucleic acid, and a circular nucleic acid molecule.

13. The method of claim 12, wherein said single-stranded template nucleic acid is protected by a phosphorothioate bond.

14. A method for reducing steric hindrance resulting from a product of a nucleic acid polymerase reaction, said method comprising conducting said nucleic acid polymerase reaction in the presence of an enzyme selected from the group consisting of an exonuclease, an endonuclease, and a uracil-DNA glycosylase, wherein said nucleic acid polymerase reaction includes a template nucleic acid, and wherein said enzyme modifies said product but does not modify said template nucleic acid, wherein said enzyme is a uracil-DNA glycosylase and the polymerase reaction further comprises uracil-containing nucleotides and terminal-phosphate-labeled thymine-containing nucleotides.

15. The method of claim 14, further comprising the step of hydrolyzing abasic sites created by removal of uracil residues from said product by said uracil-DNA glycosylase.

16. The method of claim 15, wherein said polymerase reaction is performed in the presence of at least one polyamine.

17. The method of claim 15, wherein said polymerase reaction is performed in the presence of at least one AP endonuclease.

18. The method of claim 1, wherein said template nucleic acid is immobilized within a zero mode waveguide.

19. The method of claim 1, wherein said nucleic acid polymerase reaction is conducted in a volume of less than one attoliter.

20. A method of determining a nucleotide sequence of a template nucleic acid comprising the steps of:
  a. conducting a nucleic acid polymerase reaction in the presence of a set of detectable terminal-phosphate-labeled nucleotides and an enzyme selected from the group consisting of an exonuclease, an endonuclease, and a uracil-DNA glycosylase, wherein:
    i. said reaction results in addition of nucleotides from said set of detectable terminal-phosphate-labeled nucleotides to a nascent nucleic acid strand, and
    ii. said reaction results in production of labeled polyphosphates that are released from said nucleotides from said set of detectable terminal-phosphate-labeled nucleotides; and b. sequentially identifying during said nucleic acid polymerase reaction said labeled polyphosphates or said nucleotides from said set of detectable terminal-phosphate-labeled nucleotides that yield said labeled polyphosphates in said reaction, thereby determining said nucleotide sequence of said template nucleic acid, wherein said template nucleic acid comprises a modification such that said enzyme is unable to modify said template nucleic acid.

21. The method of claim 20, wherein said enzyme is an exonuclease or an endonuclease that cleaves said nascent nucleic acid strand but does not cleave said template nucleic acid.

22. A method of determining a nucleotide sequence of a template nucleic acid comprising the steps of:
   a. conducting a nucleic acid polymerase reaction in the presence of a set of detectable terminal-phosphate-labeled nucleotides and a uracil-DNA glycosylase and the set of detectable terminal-phosphate-labeled nucleotides comprises terminal-phosphate-labeled uracil-containing nucleotides, wherein:
      i. said reaction results in addition of nucleotides from said set of detectable terminal-phosphate-labeled nucleotides to a nascent nucleic acid strand, and
      ii. said reaction results in production of labeled polyphosphates that are released from said nucleotides from said set of detectable terminal-phosphate-labeled nucleotides; and
   b. sequentially identifying during said nucleic acid polymerase reaction said labeled polyphosphates or said nucleotides from said set of detectable terminal-phosphate-labeled nucleotides that yield said labeled polyphosphates in said reaction, thereby determining said nucleotide sequence of said template nucleic acid.

23. The method of claim 22, further comprising the step of hydrolyzing abasic sites created by removal of uracil residues from said nascent nucleic acid strand by said uracil-DNA glycosylase.

* * * * *